| United States Patent [19] | [11] Patent Number: 4,574,080 |
| --- | --- |
| Roswall et al. | [45] Date of Patent: Mar. 4, 1986 |

[54] COMBINATION FORMULATION

[75] Inventors: Stig Roswall, Soborg; Lene B. Thorhus, Holte, both of Denmark

[73] Assignee: A/S Alfred Benzon, Copenhagen, Denmark

[21] Appl. No.: 523,635

[22] Filed: Aug. 15, 1983

[30] Foreign Application Priority Data

Aug. 13, 1982 [DK] Denmark .............................. 3652/82

[51] Int. Cl.$^4$ .......................... A61K 9/22; A61K 9/48; A61K 9/50; A61K 9/54
[52] U.S. Cl. ....................................... 424/20; 424/22; 424/31; 424/32; 424/33; 424/34; 424/35; 424/36; 424/37; 424/38; 424/153; 427/3
[58] Field of Search ..................................... 424/31-38, 424/149, 153, 20, 22; 427/3

[56] References Cited

U.S. PATENT DOCUMENTS

| 3,873,346 | 3/1975 | Sweeny et al. .......................... 427/3 |
| --- | --- | --- |
| 3,909,444 | 9/1975 | Anderson et al. ........................ 427/3 |
| 4,173,626 | 11/1979 | Dempski et al. ....................... 424/19 |
| 4,259,315 | 3/1981 | Lippmann et al. ................... 424/153 |
| 4,316,884 | 2/1982 | Alam et al. ............................ 424/19 |
| 4,322,449 | 3/1982 | Voss et al. ............................... 427/3 |
| 4,353,887 | 10/1982 | Hess et al. .............................. 424/19 |
| 4,359,483 | 11/1982 | Kaetsu et al. ............................ 427/3 |
| 4,411,933 | 10/1983 | Samejima et al. ..................... 424/19 |

FOREIGN PATENT DOCUMENTS 1468172 3/1974 United Kingdom .

OTHER PUBLICATIONS

Bechgaard, H., Hegermann Nielsen, G. & Aggerbeck, A. (1979) Kalinorm. en Polydepot Tablet Med Kontrolleret Udlosning AF Kaliumklorid. in vitro og in vivo-Dokumentation. Farm, TID, 89; 761-766.
Brophy, M. R. & Deasy, P. B., Influence of Coating and Core Modifications on the in vitro Release of Methylene Blue from Ethylcellulose Microcapsules Produced by Pan Coating Procedure, J. Pharm. Pharmacol, 33 (1981), pp. 495-499.
Harris, M. S., Preparation and Release Characteristics of Potassium Chloride Microcapsules, J. Pharm., 70 (1981), 391-394.

(List continued on next page.)

Primary Examiner—Ronald W. Griffin
Attorney, Agent, or Firm—Stiefel, Gross, Kurland & Pavane

[57] ABSTRACT

A pharmaceutical oral controlled release multiple-units formulation is prepared by mixing units containing an active substance and coated with a substantially water-insoluble, but water diffusable controlled release coating with particles of an active substance, the mean size of which is at least one power of 10 smaller than the coated units under conditions which will result in adherence of the smaller particles to the surface of the controlled release coating in a substantially uniform layer. The coated units have a mean size of between about 0.1 and 1.5 mm, in particular about 0.4 to 1.2 mm, and the fine particles have a mean particle size of from about 1 to about 50 μm and are present in the composition in an amount of at the most 25 percent by weight, in particular at the most 5 percent by weight and preferably not more than 1 percent by weight, calculated on the weight of the coated units. The mixing is performed in the presence of an anti-adhesive which counteracts undesired electrostatic charging such as talc or colloidal silicon dioxide. The active substance which is subject to controlled release may be potassium chloride, and the active substance of the small particles may be a diuretic.

The controlled release coating contains a film-forming polymer such as ethyl cellulose, a plasticizer and a hydrophobic substance.

In this manner, it is possible to combine an active substance which it is preferred to administer in a controlled release multiple-units composition, for example because it has an irritating effect on the gastric mucosa or because it has a short half life, with an instantly releasing active substance to obtain a combination composition which simplifies the dosing regimen and thus improves patient compliance.

29 Claims, 3 Drawing Figures

OTHER PUBLICATIONS

Statistical Methods Applied to Experiments in Agriculture and Biology by George W. Snedecor (Fifth Edition).

Propoxyphene and Norpropoxyphene: Influence of Type of Controlled-Release Formulation on Intra- and Intersubject Variations (1980), by Helle Bechgaard et al.

Influence of Food on the Absorption of Acetylsalicylic Acid from Enteric-Coated Dosage Forms (1978), by C. Bogentoft et al.

Tablets of Coated Aspirin Microspherules-A New Dosage Form by D. M. Green, M.D.

McDonald, P. J., Mather, L. E. & Story, M. J. (1977) Studies on Absorption of a Newly Developed Enteric-Coated Erythromycin Base., J. Clin. Pharmacol 17, 601-606.

Pharmaceutical Dosage Forms, Tablets, Eds. Lieberman, H. A. and Lachman, L., vol. 2, Marcel Dekker, Inc., New York, 1981.

Content and Dissolution Uniformity Testing of Controlled Release Products-The Repro-Dose Quality Control Procedure by Steen Baggesen et al., pp. 85-91.

Controlled-Release Multiple-Units and Single-Unit Doses-A Literature Review-Helle Bechgaard et al., (1978), pp. 53-67.

Distribution of Pellets in the Gastrointestinal Tract, The Influence on Transit Time Exerted by the Density or Diameter of Pellets, (1978), by Helle Bechgaard et al.

COMBINATION FORMULATION

The present invention relates to an oral pharmaceutical controlled release multiple-units dosage form with important new features.

TECHNICAL BACKGROUND

Many physiological factors influence both the gastrointestinal transit time and the release of a drug from a controlled release dosage form and thus the uptake of the drug into the systemic circulation. Dosage forms should therefore be designed so that such variable factors do not compromise the efficacy and safety of the product.

In humans, a reproducible gastrointestinal transit time of a depot formulation can be achieved only by a controlled release multiple-units dosage form.

The term "controlled release multiple-units formulation" (Bechgaard & Hegermann Nielsen, 1978) indicates a pharmaceutical formulation comprising a multiplicity (typically at least 100) of individual coated (or "microencapsulated") units contained in the formulation in such a form that the individual units will be made available from the formulation upon disintegration of the formulation in the stomach of animals, including humans, who have ingested the formulation. Typically, the multiple-units formulation may be a capsule which disintegrates in the stomach to make available a multiplicity of individual coated units contained in the capsule, or a tablet which disintegrates in the stomach to make available a multiplicity of coated units originally combined in the tablet.

Drug release from a controlled release dosage form is generally controlled either by diffusion through a coating or by erosion of a coating by a process dependent on, e.g., enzymes or pH. The importance of a pH independent diffusion with respect to obtaining a reproducible rate of availability and to minimizing intra- and intersubject variations is known (Great Britain Pat. No. 1 468 172 and Bechgaard & Baggesen, 1980). It is also known that controlled drug release in vivo can be achieved through an erodable process by enteric coating of a multiple-units dosage form (Green, 1966; McDonald et al., 1977; Bogentoft et al., 1978).

Both above-mentioned types of controlled release multiple-units formulation techniques aim at a controlled release of active substance in a predetermined pattern to reduce and delay the peak plasma concentration without affecting the extent of drug availability. Due to a lower peak plasma concentration, the frequency of undesirable side-effects may be reduced, and due to the delay in the time it takes to obtain the peak plasma concentration and the prolongation of the time at the therapeutically active plasma concentration, the dosage frequency may be reduced to a dosage taken only twice or once daily, in order to improve patient compliance.

A further advantage of the controlled release multiple-units dosage form is that high local concentrations of the active substance in the gastrointestinal system is avoided, due to the units being distributed freely throughout the gastrointestinal tract, independent of gastric emptying. If the mucosa of the stomach is more sensitive to the active substance than the intestinal mucosa, controlled release formulations avoiding release of active substance in the gastric area will be preferred; formulations of this type are controlled release multiple-units formulations in which the coatings are substantially resistant to gastric conditions.

The present invention deals with multiple-units dosage forms which comprise a combination of two active substances one of which is diffusion coated.

There are cases where it is desired to combine two active substances, either to obtain a combination effect or to improve patient compliance. Thus, e.g., the use of a combination of a diuretic with potassium chloride is known. Known combination products of this kind are based on a single-unit controlled release potassium chloride tablet combined with an outer layer of an instant release diuretic. In the known art preparation of diffusion-coated controlled release multiple-units formulations, diffusion film-coating mixtures have been used which contain synthetic film-forming agents dissolved or dispersed in organic solvents, e.g. isopropanol, ethanol, acetone, or mixtures thereof. However, in particular when the units contain a readily soluble active substance, it has been often difficult to obtain a sufficiently slow release of the active substance.

DISCLOSURE OF INVENTION

Figure 1:
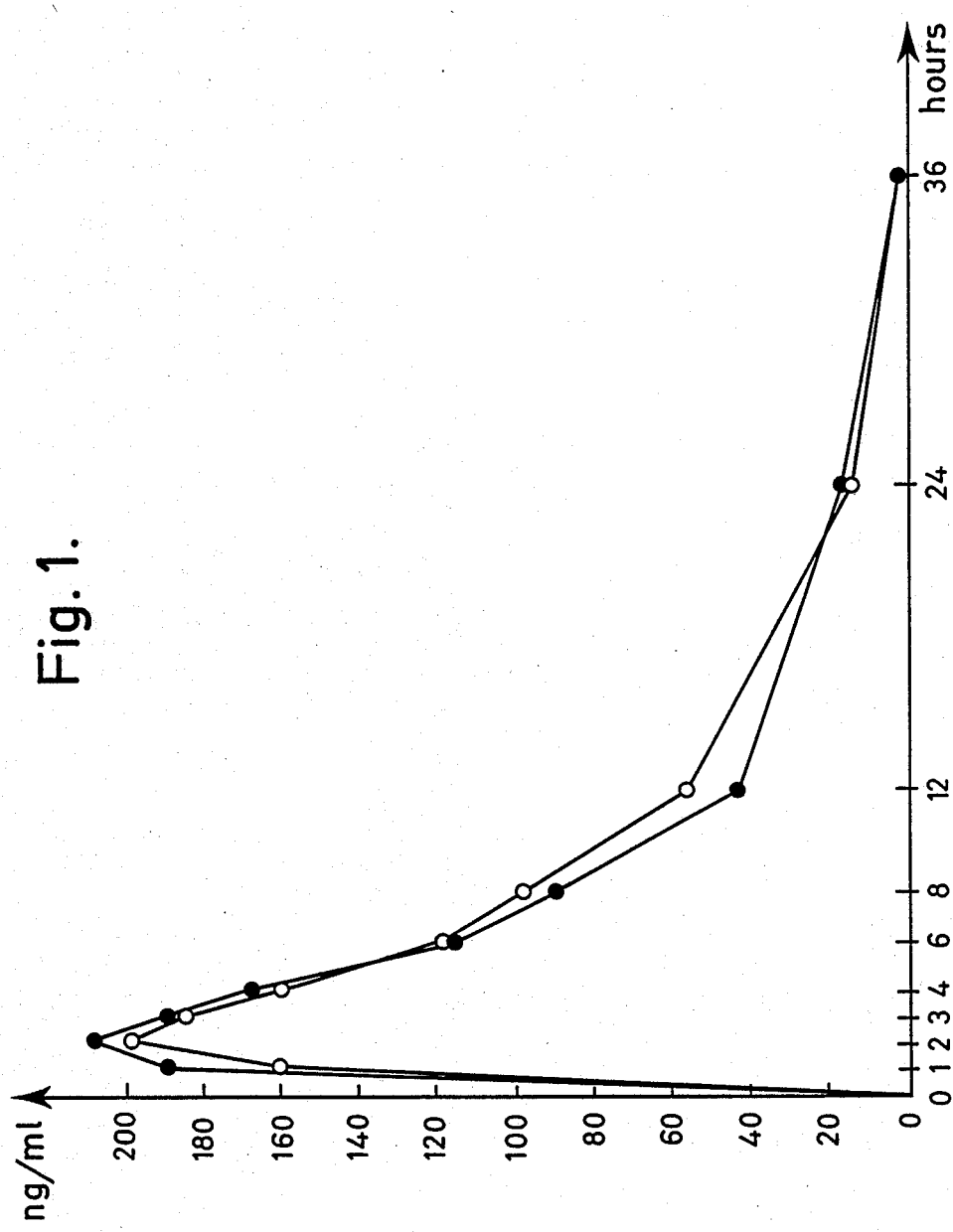
FIG. 1 graphically shows drug release.
Figure 2:
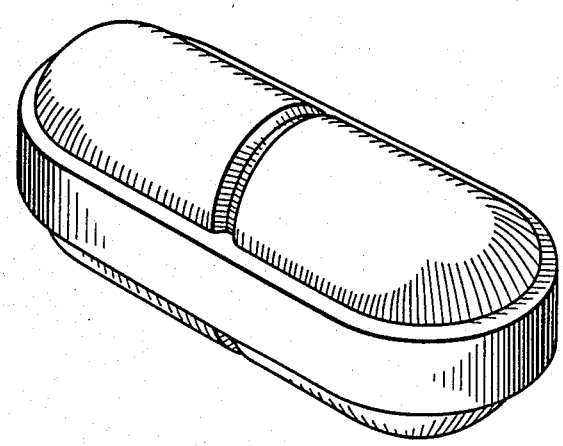
FIGS. 2 and 3 illustrate examples of the divisible tablet according to the invention.
Figure 3:
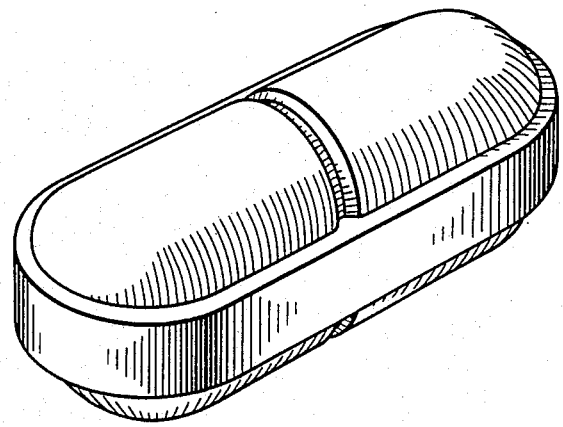

The present invention provides a pharmaceutical oral controlled release multiple-units formulation or dosage form in which individual units comprise coated units containing an active substance which is subject to controlled release as a result of coating of the units with a water-insoluble, but water diffusible controlled release coating, the units additionally comprising particles of an active substance adhered to the surface of the controlled release coating in a substantially uniform layer, the particles being at least one power of ten smaller than the coated units.

As mentioned above, there are cases where it is desired to combine an active substance subject to controlled release with an active substance which is not subject to controlled release.

There are several methods known in the art for obtaining such a combination. However, when the substance which is to be subject to controlled release is present in units, the weight of which is relatively large compared to the weight of the instant release substance which is to accompany the controlled release substance, problems arise. Thus, e.g., an unacceptable content uniformity of the low dose instant release component is experienced. It is not easy or may even be impossible to obtain a sufficiently homogeneous mixture of the two components; even if a homogeneous mixture has been obtained, later manipulation of the mixture may result in partial de-mixing with consequent variation of the ratio between the components. Hence, known art methods for combining two active substances are not always satisfactory in such a case. For instance, one method would be to distribute the minor component on the exterior of the controlled release-coated major component from a solution. However, this method cannot be used when the minor component is not sufficiently soluble in solvents which might otherwise be acceptable or suitable for such a procedure. Another possibility would be to suspend the minor component in the controlled release coating applied on the major component. However, it is not easy to control the amount of the minor component applied in this manner, and the minor component, when incorporated in the controlled release coating, may adversely influence the sustained release properties of the coating and, in addition, the minor component may lose its instant release characteristics. The application of a solution on a controlled release coating already formed on the major component might dissolve part of the coating on the major component and thus adversely influence the controlled release characteristics designed for the major component.

According to the present invention, pharmaceutical oral controlled release multiple-units formulations are prepared by mixing units containing an active substance and coated with a substantially water-insoluble, but water diffusible controlled release coating, with particles of an active substance the mean size of which is at least one power of ten smaller than the coated units, under conditions which will result in adherence of the smaller particles to the surface of the controlled release coating in a substantially uniform layer.

As mentioned above, the mixing of the coated units with the smaller particles is performed under conditions which will result in adherence of the smaller particles to the surface of the controlled release coating in a substantially uniform layer. This mixing is of the type of the so-called ordered mixing where mechanical, adhesional, or coating forces or methods are used to prepare an ordered unit in a mix such that the ordered unit will be the smallest possible sample of the mix and will be nearly identical in composition to all other ordered units in the mix (cf., e.g, Lieberman & Lachman, 1981). Through the method of the invention, it has thus become possible to obtain a stable composition with an acceptable content uniformity which permits the dosing of the resulting units as capsules, in sachets, or as tablets, without any segregation or de-mixing problems occurring during handling of the compositions.

In the formulation according to the invention, the active substance adhered to the surface of the controlled release coating is present in an amount of no more than about 25% by weight, preferably no more than about 10% by weight, in particular no more than about 5% by weight, especially no more than about 2% by weight, and preferably no more than 1% by weight such as 0.5–1% by weight, calculated on the weight of coated units.

In most cases, the formulation of the invention will additionally comprise an anti-adhesive adhered to the coated units. The anti-adhesive is normally a fine particle powder which counteracts electrostatic charging.

As examples of anti-adhesives may be mentioned colloidal silicon dioxide, talc, metallic stearates, starches such as rice starch, stearic acid, etc. The function of the anti-adhesive is to improve the flow characteristics of the powder, to prevent the fine particles from adhering to each other, and to prevent the fine particles from adhering to the mixer walls, etc.

The amount of anti-adhesive should be adapted in accordance with the particular coated units, the particular particles which are to be adhered to the surface of the coated units, the mixing equipment, etc. As a general rule, as little anti-adhesive should be used as possible, in order to avoid the undesired effect that the anti-adhesive will prevent the particles of active substance from adhering to the coated units. Typical amounts of anti-adhesive are amounts of about the same order of magnitude as the active substance itself, but variations of at least one power of ten downward and possibly even lower are also within the scope of the invention. The dry coating or mixing process according to the invention may be performed by means of any usual suitable type of mixing equipment such as low shear mixer, including cone and cube mixers, and the characteristic way of performing the mixing is to mix for a sufficient period of time to obtain a steady state condition where there is substantial equilibrium between the amount of fine powder that is adhered to the larger units and the amount of fine particles which leave the larger units. A condition for obtaining the steady state is that the relative amounts of the fine particles and the larger units are suitably adapted. If a too large amount of fine particles were present, the steady state condition and the uniform adherence to the coating on the larger particles would not be obtained. The assessment of suitable ratios may easily be performed by the skilled art worker through preliminary tests.

The water-insoluble, but water-diffusible controlled release coating may be a coating of a known type which is prepared by application of diffusion film-coating mixtures which contain synthetic film-forming agents dissolved or dispersed in organic solvents, e.g. isopropanol, ethanol, acetone, or mixtures thereof. However, in particular when the units contain a readily soluble active substance, it has often been difficult to obtain a sufficiently slow release of the active substance.

According to a particular aspect of the present invention, the controlled release coating is of the type which is applied from an organic solvent as described above, but which has been made to release its content of active substance over a longer period of time.

Thus, it has been found that addition of a hydrophobic substance to a coating mixture containing a film-forming polymeric substance and application of the coating mixture under special conditions, that is, by applying the coating mixture on the units at a temperature above the melting temperature of the hydrophobic substance, will result in a coating which delays and controls the diffusion through a coating of the polymer film in a useful and reproducible manner to confer desirable controlled release characteristics to the coated units. Thereby, film forming polymers which in themselves are diffusion-controlling to an insufficient extent are improved to obtain a more efficient diffusion control.

This measure is of particular importance in connection with the coating of substances which exert a local irritating effect on the mucosa of the gastrointestinal tract such as potassium chloride.

Thus, in a preferred formulation according to the invention, the controlled release coating contains a film-forming substance, a plasticizer, and a hydrophobic substance.

The film-coating mixture of the above type is prepared and applied under such conditions that the hydrophobic substance must be considered to be effectively microdispersed in fluid condition throughout the coating solution.

It is presumed that the controlled evaporation conditions during the fluid bed application, combined with the fact that the hydrophobic substance is in a molten, but undissolved and microdispersed state results in a more uniform distribution of the hydrophobic substance in the final dry film coating than when the hydrophobic substance is in a dissolved state and precipitates from the dissolved state.

The film-forming polymeric substances used for this type of coating mixtures are pharmaceutically acceptable film-forming polymers which are substantially water-insoluble, but which permit water diffusion. Examples of such substances are cellulose derivatives, for instance ethylcellulose, acrylic polymers, vinyl polymers, and other high molecular synthetic polymers such as ethylcellulose, cellulose acetate, cellulose propionate, cellulose butyrate, cellulose valerate, cellulose acetate propionate, polyvinyl acetate, polyvinyl formal, polyvinyl butyral, ladder polymer of sesquiphenyl siloxane, polymethyl methacrylate, polycarbonate, polystyrene, polyester, coumarone-indene polymer, polybutadiene, vinyl chloride-vinyl acetate copolymer, ethylene-vinyl acetate copolymer and vinyl chloride-propylene-vinyl acetate copolymer. The hydrophobic substance incorporated may be any pharmaceutically acceptable hydrophobic substance which will result in the desired retardation of the diffusion (in the present context, the term "hydrophobic" indicates substances which, relative to water, have a contact angle of more than 90°). All such hydrophobic substances are substances which, by themselves, that is, without admixture with other components, are capable of forming a continuous phase (that is, either by being molten or by being dissolved and subjected to removal of the solvent). The amount of the hydrophobic substance incorporated will depend on the properties of the hydrophobic substance, in particular its hydrophobicity, with respect to delaying the water diffusion of the polymeric film.

Typical examples of such hydrophobic substances are substances selected from hydrocarbons and hydrocarbon derivatives, waxes, oils and fats, and mixtures thereof.

One class of hydrophobic substances which are interesting for the purpose of the present invention are wax-like substances. Examples of wax-like substances are beef tallow, whale wax, beeswax, solid paraffin, castor wax, and higher fatty acids such as myristic, palmitic, stearic and behenic acids and esters thereof.

The hydrophobic substances will usually have a melting temperature below 100° C.

The hydrophobic substance, e.g. a waxy substance such as paraffin wax, will normally be present in the coating in an amount of between about 1 and 25%, in particular between 3 and 20%, especially between about 5 and 18%, such as between about 9 and about 17%, calculated on the weight of the dry matter of the coating suspension.

As mentioned above, the diffusion coatings applied from an organic solvent also comprise a plasticizer. As examples of plasticizers may be mentioned triacetin, acetylated monoglyceride, rape oil, olive oil, sesame oil, acetyltributylcitrate, acetyltriethylcitrate, glycerin, sorbitol, diethyloxalate, diethylmalate, diethylfumarate, diethylsuccinate, diethylmalonate, dioctylphthalate, dibutylsebacate, triethylcitrate, tributylcitrate, glycerolitributyrate, polyethyleneglycol, propyleneglycol, and mixtures of the above.

The plasticizer is normally used in an amount of less than 1% by weight, calculated on the weight of the dry matter of the coating mixture.

The individual units of the multiple-units formulations according to the invention will normally be either coated crystals or pellets (coated cores). In the pellets, the core is constituted by a combination of active substance and excipients. A type of core which is widely used in the known art (vide, e.g., Eur. Patent Application No. 79850 110) is a substantially spherical particle of a size of about 0.5–1 mm consisting of excipient(s) with active substance applied to its surface. Typical cores of this type are the so-called "non-pareil" cores where the excipients are in the form of spherical particles of saccharose. It is also known, e.g., from Great Britain Patent Specification No. 1 468 172, to prepare cores which are cross-sectionally substantially homogeneous. In the present context, the term "cores which are cross-sectionally substantially homogeneous" designates cores in which the active substance is not confined to an exterior layer on the core body, in other words normally cores which, through the cross-section of the core body, contain substantially the same type of composition comprising microparticles containing active substance, in contrast to the non-pareil type of cores which each consist of an excipient body with active substance applied to its surface, and in contrast to coated crystal units which are substantially monolithic crystals. From this definition, it will be understood that the cores which are cross-sectionally substantially homogeneous will normally consist of a mixture of active substance with excipient(s), (and in spite of the term "homogeneous", this mixture will not necessarily be qualitatively or quantitatively homogeneous through the cross-section of the particle but may show, e.g., a concentration gradient of one or more of its constituents) or they may consist substantially solely of active substance in a non-monolithic form, e.g. as a sintered mass of crystalline or amorphous particles of active substance. In the following specification and claims, such cores which are cross-sectionally substantially homogeneous will, for the sake of brevity, often simply be designated "cores".

According to a particular aspect of the invention, diffusion-coated cores containing a medicament substance which has a pH-dependent solubility comprise a buffer substance which, in accordance with the principles disclosed in Great Britian Pat. No. 1 468 172, serves to establish a controlled pH interval inside the pellets during passage of the pellets through the gastrointestinal system, thereby securing that the medicament substance in the cores will be dissolved under controlled pH conditions.

The pharmaceutical oral controlled release multiple-units formulation according to the invention will typically be a capsule containing a multiplicity of the units, typically more than 100, a sachet containing a multiplicity of the units, typically more than 1000, or a tablet made from a multiplicity of the units, typically more than 100, in such a manner that the tablet will disintegrate substantially immediately upon ingestion in the stomach into a multiplicity of individual units which are distributed freely throughout the gastro-intestinal tract.

The formulations mentioned above may be prepared by conventional methods known in the pharmaceutical industry. One particularly interesting shape of a tablet according to the invention, in particular when the tablet is to contain a rather large amount of active substance and is to be easy to swallow, is a shape substantially corresponding to a cylinder with rounded ends, a raised area circumscribing the periphery of the cylinder in the form of flat belt and a score dividing the cylinder, but not the peripheral belt, into two parts, substantially as shown in the drawing. As an example of such tablets may be mentioned tablets in which the controlled release coated active substance is potassium chloride crystals and the instant release active substance is a diuretic, e.g. in tablet sizes comprising 600 mg of potassium chloride and 5 mg of clopamide for patients in diuretic treatment to prevent potassium deficiency.

DETAILED DESCRIPTION OF INVENTION

Cores

According to the invention, the cores are preferably cross-sectionally substantially homogeneous cores. The use of cross-sectionally substantially homogeneous cores offers several advantages.

Firstly, it is easy to produce cross-sectionally substantially homogeneous cores reproducibly on a large scale, for instance by means of automatic equipment, because the components therefor are normally simply mixed in the prescribed proportions, which means that inter-core variations in composition, e.g., concentration of active substance, can be kept within narrow limits. Secondly, the concentration of active substance in the core can be varied within very wide limits (generally between 1 and 90% by weight), which renders it possible to optimize the concentration of active substance in the single core in order to minimize capsule axis for a given dosage strength and thereby optimize patient compliance. Thirdly, the size of the cores may be easily adjusted as desired, to improve the distribution pattern of the units throughout the gastrointestinal tract; this forms a contrast to the non-pareil technique where the size variation is limited by the available standard sizes. Fourthly, the composition of the cores may be optimized with respect to the extent of drug availability, i.e., to enhance the release of the active substance.

The cores are typically made by granulating particles of the active substance together with excipients, including bulk agents such as carbohydrates and derivatives thereof such as starch and starch derivatives, including microcrystalline cellulose, binders such as cellulose derivatives, including methylcellulose or hydroxypropylmethylcellulose, polyethylene glycol, polyvinylpyrrolidone, agar, or gelatin, for instance by treatment in a high speed mixer (to directly obtain compact-shaped cores), or by treatment in a planet mixer with subsequent extrusion of the mixture into strings of a predetermined diameter approaching the desired final cross-sectional dimension of the cores and treatment of the strings in a marumerizer or similar equipment to obtain compact-shaped cores. The diameter of the cores is normally adapted so that the diameter of the coated core is about 0.4–1.2 mm, in particular about 0.5–1.0 mm, especially about 0.5–0.8 mm, such as 0.5–0.7 mm. A preferred diameter of the coated cores is about 0.5–0.6 mm.

In accordance with a particular aspect of the invention, the predetermined controlled release of the active substance may be changed by changing the density of the cores, and thus, the time of arrival of the cores in the predetermined section of the intestine may be varied at will. By increasing the density of the cores with resulting increased transit time of the coated cores (Bechgaard & Ladefoged, 1978), a more delayed and longer lasting absorption phase is obtained, that is, a longer period during which the absorption of the active substance takes place after the substance has been released by diffusion of the coating, thus having become available for absorption.

Examples of excipients which may be used to increase the density of the cores are described in U.S. Pat. No. 4,193,985 and include heavy particulate substances such as barium sulphate, titanium oxide, zinc oxides, and iron salts.

According to another particular aspect of the invention, a buffer substance is incorporated in the core when the medicament substance is one which has a pH-dependent solubility. The buffer or buffer mixture is preferably so selected that the buffered system in the cores obtains a pH between 1 and 7.5, in particular a pH in the range from about 4 to about 6. The amount of buffer should be sufficient to obtain a buffer effect during the period necessary for the release of the active substance and may easily be determined by the skilled art worker through simple tests. As examples of suitable pharmaceutically acceptable buffer substances may be mentioned primary, secondary or tertiary salts of phosphoric acid or salts of phthalic acid, citric acid, tartaric acid, or salts of aminoacids such as glycine, or mixtures of such buffer salts. A typical concentration of buffer substance in the cores is in the range of from about 3 to about 40% by weight, calculated on the core constituents, preferably from about 5 to about 30% by weight.

Crystals

When the units coated according to the invention are crystals, they normally have a size between about 0.2 and 1.5 mm, preferably between about 0.2 and 0.6 mm. As an important example of an active substance which is suitably used in the form of crystals, potassium chloride may be mentioned.

Active Substance

The active substances in the combination formulations according to the invention may be any active substances which are advantageously administered in a controlled release multiple-units formulation and the other active substance is available as an instant release active substance. Examples of suitable active substances incorporated in the controlled release unit are found among almost all therapeutic groups, including diuretics, $\beta$-blockers, vasodilators, analgesics, bronchodilators, hormones, oral antidiabetics, antihypertensives, antibiotics, and potassium chloride.

Examples of suitable active substances used as the instant release drug in the combination formulations are found among almost all therapeutic groups, including diuretics, $\beta$-blockers, vasodilators, analgesics, bronchodilators, hormones, oral antidiabetics, antihypertensives, and antibiotics.

Preferred combinations of the above-mentioned components of the combination product may be found among controlled release coated potassium chloride units such as crystals, and instant release diuretics such as metolazone, clopamide, ethacrynic acid, hydroflumethiazide, methyclothiazide, quinethazone, trichloromethiazide, chlorothiazide, chlorothalidone, cyclothiazide, furosemide, hydrochlorothiazide, polythiazide, bendroflumethiazide, cyclopenthiazide, mefruside, and bumetanide.

Among active substances which are advantageously controlled release coated, some are characterized as having a pH-dependent solubility, others as having a pH-independent solubility.

As examples of active substances which have a pH-dependent solubility (that is, a solubility which differs corresponding to a ratio of $10:10^3$ over the physiological pH range of 1–7.5) may be mentioned pindolol, lithium carbonate, acemetacin, vincamine, dipyridamol, theophyllin, dextropropoxyphen, furosemide, and hydralazin.

Active substances having a pH-dependent solubility are preferably incorporated in cores in combination with buffer substances such as discussed above, in order to obtain a dissolution of active substance which is substantially independent of the gastrointestinal pH variations through which the units pass.

As examples of active substances with a solubility which is not pH-dependent may be mentioned propranolol and atenolol.

Especially important formulations according to the invention are formulations in which the active substance, apart from being a substance about which it is known or indicated from a pharmacokinetic and/or clinical point of view that it is advantageously administered in a controlled release multiple-units formulation, is a substance which exerts an irritating effect on the gastric mucosa such as acetylsalicylic acid, potassium chloride, and which is usually administered concomitantly to an active substance such as a diuretic.

The invention also makes it possible to combine two active substances with significantly different half lives in order to harmonize the duration of time above a therapeutically active plasma level. The active substance with the shorter half life should be incorporated in the controlled release coated units, and the active substance with the longer half life should be used as the instant-release substance, thus simplifying dosage regimen and improving patient compliance by administering only one type of tablet or capsule.

Coating

The diffusion coating applied on the units according to the invention is applied either from a solution and/or suspension in an organic solvent or from an aqeous coating mixture. The application from a solution and/or suspension in an organic solvent will be discussed first.

As examples of suitable solvents may be mentioned alcohols such as ethanol, methanol, isopropanol, and propanol, ketones such as acetone, and toluene. The application of the coating is performed in a fluidized bed or by pan coating; application in a fluidized bed is preferred.

Examples of diffusion coating materials which may be used for the purpose of the present invention are mentioned above. Preferred coating materials are cellulose derivatives such as, e.g., ethylcellulose, and acrylic polymers such as polymethylmethacrylate, e.g., the so-called Eudragit ® coatings.

The coating material may be admixed with various excipients such as plasticizers, inert fillers, and pigments, in a manner known per se.

The amount of coating applied is adapted so as to obtain a predetermined dissolution characteristic of the coated units. Normally, the amount of the coating will be about 0.5–25% by weight, calculated as dry matter on the total weight of the units, typically about 1–15% by weight, depending on the predetermined dissolution characteristics of the active substance and the desired release profile.

The diffusion coating applied on the units according to the invention may also be a diffusion coating which is applied from a solution and/or suspension in water. The application of the coating is typically performed in a fluidized bed or by pan coating.

Examples of such water-based diffusion coating materials which may be used for the purpose of the present invention are coatings selected from the group consisting of acrylic polymers and copolymers, e.g., a polymerisate of acrylic acid ethyl esters and methacrylic acid methyl ester such as Eudragit ®E 30 D or ethylcellulose such as Aquacoat ®ECD-30.

The coating material may be admixed with various excipients such as plasticizers, inert fillers, and pigments, in a manner known per se.

Examples of plasticizers are the same as mentioned in connection with the organic solvent-based coating mixtures.

The amount of coating applied from a water-based coating mixture is adapted so as to obtain a predetermined dissolution characteristic of the coated units. Normally, the amount of the coating will be about 2–25% by weight, calculated as dry matter on the total weight of the units, typically about 15% by weight, depending on the predetermined dissolution characteristics of the active substance of the desired release profile.

Dosage forms

The units prepared according to the invention may be incorporated in normal pharmaceutical dosage forms or formulations such as capsules containing a multiplicity of the units, sachets containing a multiplicity of the units, or tablets which will disintegrate substantially immediately upon ingestion in the stomach to form a multiplicity of individual units.

The adjuvants and excipients used in the preparation of disintegratable tablets are of the same kind as conventionally used in the pharmaceutical industry for this purpose. Examples of filler or diluents useful for preparing tablets according to the invention are lactose, sucrose, dextrose, mannitol, calcium sulphate, dicalcium phosphate, tricalcium phosphate, starches such as rice starch and microcrystalline cellulose. Useful binders are acacia, tragacanth, gelatine, sucrose, pregelatinized starch, starch, sodium alginate, ammonium calcium alginate, methylcellulose, sodium carboxymethylcellulose, ethylcellulose, hydroxypropylmethylcellulose, polyvinylpyrrolidone, magnesium aluminum silicate, and polyacrylamides. As examples of disintegrants may be mentioned starches and starch derivatives, clays, and celluloses including microcrystalline cellulose, alginates and gums, including agar, and tragacanth. As "lubricants", "glidants" and "anti-adherents" may be mentioned metallic stearates, talc, high melting point waxes, and colloidal silicon dioxide.

When it is desired to use excipients or adjuvants for the preparation of sachets or capsules, such as fillers and lubricants, these may be of the same type as described above.

The filling of capsules and sachets and the compression of tablets are performed by manners known per se.

MATERIALS AND METHODS

| | |
|---|---|
| Clopamide: | 4-chloro-N—(cis-2,6-dimethylpiperidino)-3-sulfamoyl-benzamide supplied by Sandoz AG, Basel, Switzerland. Purity 98.0–102.0%, ground to particle size of approximately 8 μm. |
| Potassium chloride: | Ph.Eur. fraction, 0.2–0.6 mm. |
| Isopropanol: | BP 80 |
| Paraffin: | NF XV |
| Acetyltributylcitrate: | Citroflex ® A4; supplied by Pfizer A/S, Copenhagen, Denmark. |
| Ethylcellulose: | NF XV |
| Colloidal silicon dioxide: | USP XX |
| Magnesium stearate: | Ph.Eur. |
| Microcrystalline | BPC 79 |

| cellulose: | |
|---|---|
| Rice starch: | Ph.Eur. |
| Talc: | Ph.Eur. |

Determination of the Quantity of Clopamide Adhered to the Film-Coated KCl-Crystals After a Mechanical Stress A sample containing film-coated KCl-crystals with clopamide adhered to the surface was placed on a sieve. The mesh of the sieve had a size of 212 μm preventing the film-coated KCl-crystals from passing, but allowing any other part of the sample to pass.

The sieve and sample were shaken (Pascal sieve, model 1) for 15 minutes. The quantity of clopamide adhered to the film-coated crystals was then determined as described under Content Uniformity (clopamide)

Uniformity of Mass

The uniformity of mass was determined according to Ph. Eur. 2nd Ed 1., V.5.2.

Disintegration Time of Tablets

The disintegration time of tablets was measured according to Ph.Eur. 2nd Ed.1, V.5.1.1. using a disc.

Assay for Potassium Chloride

The content of potassium chloride was determined by heating 10 tablets in water until boiling.

After cooling and filtration, the filtrate was titrated with 0.1N silver nitrate, using dichlorofluorescein as the indicator.

Content Uniformity (Clopamide)

Content uniformity of clopamide is determined in 10 tablets, treating each tablet with 0.1M hydrochloric acid (pH 1.2) in an ultrasonic bath for 1 hour. The quantity of clopamide in each tablet was determined spectrophotometrically at 242 nm.

According to applicants' standards, the content uniformity of clopamide must meet the requirements for tablets stated in USP XX p 955, i.e. the content of clopamide per tablet may vary from 4.25 mg to 5.75 mg.

Determination of in Vitro Dissolution Rate of Potassium and Clopamide

In vitro dissolution rates were determined according to Baggesen et al. (1981). The rotation speed was 30±1 r.p.m., and the dissolution medium was 25 ml of 0.1M hydrochloric acid (pH 1.2), maintained at 37°±0.1° C. Release of active substance into the dissolution medium was determined by measuring the absorbance spectrophotometrically at 242 nm (clopamide) or by measuring by means of an ion-selective electrode (potassium).

Determination of Clopamide in Plasma

Concentrations of clopamide were analyzed by a HPLC method after extraction from plasma. An S5 ODS Spherisorb column was used and the mobile phase was acetonitrile:0.05N sulphuric acid 2:1. For each subject a calibration curve was made on spiked plasma, and a linearity between peak height and plasma concentration of clopamide could be revealed in the range 20 ng/ml to 500 ng/ml.

Two plasma samples spiked with clopamide to 40 ng/ml and 200 ng/ml served as quality control samples. Mean and SD based on nine different measurements: 40±7 ng/ml and 196±13 ng/ml—with no evident trend in the results.

Determination of Potassium in Urine

Potassium in urine was measured by a flame photometric method.

EXAMPLE 1

Preparation of Film-coated Potassium Chloride Crystals

Preparation of film-coating mixture

A film-coating mixture was prepared from 2.809 kg paraffin, 0.983 kg acetyl tributyl citrate, 18.433 kg ethylcellulose, 0.281 kg colloidal silicon dioxide and 372.494 kg isopropanol.

The paraffin was melted in 123 kg of the isopropanol by heating in a mixer equipped with a heating jacket at 70° C. The acetyl tributyl citrate, the ethylcellulose and the silicium dioxide were added under vigorous stirring. The vigorous stirring was continued for about 1 hour, whereupon isopropanol was added up to 395 kg, and the stirring speed was reduced. The film-coating mixture was then homogeneous and ready for use.

The film-coating mixture is used warm at approximately 70° C.

Application of Film-coating on Potassium Chloride Crystals

The film-coating mixture prepared as described above was sprayed onto 150 kg potassium chloride crystals using a fluidized bed. The potassium chloride crystals were fluidized, and the film-coating mixture was sprayed onto the crystals at a temperature of about 70° C. at a speed of about 500 g of film-coating mixture/minute. After the application of the film-coating mixture, the film-coated crystals were dried in a fluidized bed for 20 minutes, whereupon the film-coated crystals were cooled to about 20° C., while still lying in the fluidized bed.

EXAMPLE 2

Adhesion of Ground Clopamide onto Film-coated Potassium Chloride Crystals

Grinding of the clopamide to a mean particle size of about 8 μm and a maximum particle size of about 30 μm yields a suitable powder for the purpose of the present invention. This grinding may be performed by grinding the clopamide using a Fritsch Pulverisette 14, laboratory rotor-mill equipped with a 0.2 mm sieve.

Ground clopamide was coated by dry mixing onto film-coated potassium chloride crystals prepared as described in Example 1, in the presence of an anti-adhesive. The amount of clopamide adhered was determined as described under MATERIALS AND METHODS. In Table 1, the influence of the anti-adhesive and the coating time on the adhesion tendency of clopamide is shown. A designates the amount of clopamide adhered in percent of the theoretical dose (600 mg potassium chloride, 5 mg clopamide) immediately after the dry coating, B designates the percentage of the theoretical dose of clopamide adhered per dose of finished granulate prepared as described in Example 4 below, and C designates the percentage of a dose of clopamide being removed from the film-coated potassium chloride crystals during the mixing of the granulate (A-B).

TABLE 1

Influence of anti-adhesive and Coating Time on Adhesion Tendency of Clopamide

| Coating time (min.) | Anti-adhesive | | | | | | | | |
|---|---|---|---|---|---|---|---|---|---|
| | Talc (1.5 × the amount of clopamide) | | | Colloidal silicon dioxide (0.13 × the amount of clopamide) | | | anti-adhesive Talc (2.0 × the amount of clopamide) | | |
| | A (%) | B (%) | C (%) | A (%) | B (%) | C (%) | A (%) | B (%) | C (%) |
| 10 | 96.4 | 65.0 | 31.4 | 70.4 | 60.2 | 10.2 | 76.4 | 53.8 | 22.6 |
| 30 | 88.4 | 69.8 | 18.6 | 75.2 | 58.8 | 16.4 | 87.6 | 65.4 | 22.2 |
| 60 | 100.2 | 78.6 | 21.6 | 85.8 | 66.6 | 19.2 | 86.2 | 70.6 | 15.6 |

It appears from Table 1 that
an increased coating time causes an increased adhesion
an increased amount of anti-adhesive causes a reduced adhesion
when talc is used as anti-adhesive, an increased coating time causes, not only an increased adhesion, but also a more resistant adhesion, i.e. a smaller amount of clopamide is removed due to the stress applied to the system during the admixture of the auxiliary materials.

As a considerable amount of the clopamide (about 20%) is removed by the admixture of the necessary auxiliary materials for the tabletting process (vide Table 1), it was examined whether a more gentle, but more laborious method in which the auxiliary materials are premixed separately, thus reducing the final mixing time, would reduce this removal.

The results of this examination are shown in Table 2.

TABLE 2

The influence of the method of admixing of the auxiliary materials on the abraded amount of clopamide

| | Anti-adhesive: Talc (2.0 × the amount of clopamide) | | | | | |
|---|---|---|---|---|---|---|
| | Usual admixture of auxiliary materials (mixing time after dry coating = 11 min.) | | | Gentle admixture of auxiliary materials (mixing time after dry coating = 5 min.) | | |
| Coating time (min.) | A (%) | B (%) | C (%) | A (%) | B (%) | C (%) |
| 60 | 86.2 | 70.6 | 15.6 | 83.0 | 70.0 | 13.0 |

A, B and C have the same meanings as in Table 1.

The results show that the reduction of the abraded amount of clopamide (C) is so modest that there is no substantial advantage in using the more laborious method.

EXAMPLE 3

Investigations Concerning the Adhesion Mechanism

In order to examine the binding mechanism between clopamide and film-coated potassium chloride crystals, tests were carried out using a composition prepared according to Example 4 below, but in pilot scale, and as a reference, similar compositions were prepared wherein the film-coated potassium chloride crystals were substituted by non-film-coated potassium chloride crystals of the same size fraction. The examinations were carried out as described above for the examination of the adhesion tendency of clopamide, and the amount of clopamide adhered was again determined as described under MATERIALS AND METHODS; the dry coating time was 60 minutes. The results are shown in Table 3 wherein A, B and C are as described above, and D designates the relative amount of adhered clopamide abrased during the final mixing $$\frac{C \times 100}{A}.$$

TABLE 3

The Influence of the Film Coating on the Adhesion Tendency

| | A (%) | B (%) | C (%) | D (%) |
|---|---|---|---|---|
| Film-Coated Potassium Chloride Crystals | 80.4 | 66.0 | 14.4 | 17.9 |
| Non-Film-Coated Potassium Chloride Crystals | 38.0 | 23.0 | 15.0 | 39.5 |

It appears from Table 3 that the presence of the film-coating is responsible for the essential part of the adhesion, more than the double amount of clopamide being adhered to the film-coated crystals. Furthermore, it appears that the abrasion during the final mixing of the granulate is relatively greater for non-film-coated crystals, vide D in Table 3.

This shows that the presence of crystals is not sufficient to form an ordered mixture of the crystalline material and a finely ground drug. Thus, the presence of the film coating assists in forming an ordered mixture of the two components, wherein the finely ground drug is to a great extent adhered to the film-coated crystals.

EXAMPLE 4

Preparation of Tablets containing 600 mg Potassium Chloride (8 mmol) and 5 mg Clopamide Tablets were prepared from 0.5 kg clopamide, 2.64 kg talc, 69.509 kg film-coated potassium chloride crystals coated as described in Example 1, 2.40 kg microcrystalline cellulose, 18.551 kg rice starch and 2.40 kg of a 1:9 mixture of magnesium stearate and talc.

The clopamide and 1.00 kg of the talc are mixed and sieved through a 0.3 mm sieve. The mixture was combined with 7 kg coated potassium chloride crystals and mixed in a 40 liters cone blender for 3 minutes.

The obtained mixture and the rest of the coated potassium chloride crystals were transferred quantitatively to a 300 liters cone blender, and the resulting mixture was mixed for 30 minutes.

The rest of the talc was sieved through a 1.4 mm sieve into the 300 liters cone blender and was mixed for one minute. The microcrystalline cellulose and the rice starch were added, and the resulting mixture was mixed for 5 minutes. The magnesium stearate mixture was mixed with 10 kg of the mixture obtained above for 3 minutes and was added to the rest of the mixture and mixed for 5 minutes.

The tablets were compressed into tablets having a weight of 960 mg, each comprising 5 mg clopamide and 600 mg potassium chloride using a capsule-shaped punch and a pressure of 2300 kg on a conventional rotating tabletting machine. The shape of the tablets appears from the drawing.

Characteristics of the Tablets

Disintegration Time (determined as described under MATERIALS AND METHODS): 140–220 seconds. The disintegration time is well within the official requirements of a disintegration within 15 minutes when tested by this method.

Uniformity of Mass

The uniformity of mass was determined as described under MATERIALS AND METHODS

| Mean = | 963.3 mg |
|---|---|
| Standard deviation = | 8.76 mg |
| Relative variation | |
| in % = | 0.91 |
| min. = | 953.4 mg |
| max. = | 981.2 mg |

The uniformity of mass is well within the official requirements permitting a variation from 915 to 1011 mg per tablet.

Content of Uniformity (Clopamide)

| Mean = | 5.00 mg |
|---|---|
| Standard deviation = | 0.14 mg |
| Relative variation | |
| in % = | 2.80 |
| min. = | 4.78 mg |
| max. = | 5.23 mg |

This is well within the limits of Applicant's standards.

In Vitro Dissolution Rate

Clopamide—Test time: 30 minutes; Mean: 4.85 mg. Potassium chloride:

| Time | Mean (mg) | Standard Deviation (mg) |
|---|---|---|
| 1 h | 173 | 11.4 |
| 2 h | 251 | 18.6 |
| 6 h | 431 | 9.5 |

Assay for Potassium Chloride 609 mg/tablet

EXAMPLE 5

A Comparison of the Bioavailability of Clopamide and Potassium after Administration of Tablets Containing both drugs 5 mg of Clopamide and 600 mg of microencapsulated Potassium Chloride (the Formulation Prepared in Example 4) and Tablets Containing the two Drugs Separately, Respectively

Purpose of the Study

To compare the bioavailability of clopamide and potassium after administration of tablets containing the two drugs simultaneously (Adurix KCl (corresponding to Example 1)) and tablets containing the two drugs separately, and to demonstrate the diuretic effect of clopamide 20 mg.

Compared with:

Brinaldix ® Sandoz Tablets containing clopamide 20 mg Kalinorm ® Alfred Benzon Tablets containing 600 mg microencapsulated potassium chloride.

Study Design:

Complete balanced cross-over study with single dose administration.

Duration of Sampling:

Blood samples were collected 36 hours and urine samples 24 hours after administration.

Number of Subjects:

10 healthy subjects without any history of renal, hepatic, gastrointestinal or heart disease.

Sex and Age:

Seven females and three males aged from 18 to 51 years.

Dosage:

Clopamide 20 mg and potassium chloride 2400 mg (32 mEq):

| A: Invention | 4 tablets |
|---|---|
| B: Brinaldix | 1 tablet |
| plus Kalinorm | 4 tablets |

The tablets were administered at 09.00 a.m. after intake of breakfast. Two weeks' wash-out period separated the two test periods.

Special Precautions Concerning Food Intake:

Two days before drug administration and throughout the test days the volunteers were kept on a low potassium diet (less than 30 mEq) and a standardized calorie intake of about 2000 kcal per day. No tea, coffee or alcohol was allowed. For the individual person the diet was identical on all six test days (2 period of 3 days).

The day before drug aministration the volunteers were given 100 ml water every hour from 09.00 a.m. during the next 12 hours, i.e. 1300 ml water per day. The same procedure was followed on the test day.

Sampling:

Blood samples were drawn before dosing and 1, 2, 3, 4, 6, 8, 12, 24 and 36 hours after. Urine was collected quantitatively 24 hours before drug administration and 24 hours after in aliquots: 0–1 h, 1–2 h, 2–3 h, 3–4 h, 4–6 h, 6–8 h, 8–12 h, and 12–24 h.

Statistical Methods:

Data which fulfil the requirement for using parametric tests were analyzed by a three-way analysis of variance, splitting the total variation up into variations between subjects, treatment periods, treatment and residual. Logarithmic transformations of the variables have been used in appropriate cases.

Randomization tests were used for comparison of peak times. Differences between groups were tested against the $H_0$ hypothesis, that there is no difference between the treatments. 95% confidence intervals were determined for difference between treatments.

Bioavailability parameters:

The extent of availability was calculated as the ratio between $AUC_{0-36}$ for clopamide after the test and the standard preparation.

As a measure of rate of availability of clopamide from the two formulations, comparisons of individual peak plasma concentrations and time to peak were performed.

Availability of potassium was estimated by the total amounts of potassium excreted into urine during 24 hours after the administration of the two formulations.
Results:

parameter of bioavailability of potassium from the two formulations. However, no data in the present study suggest a bioinequivalence of potassium from the two formulations.

TABLE 4

| | Amounts of additional potassium excreted, ΔK-(mEq) | | | | | | | | |
|---|---|---|---|---|---|---|---|---|---|
| Subject | 0-1 | 1-2 | 2-3 | 3-4 | 4-6 | 6-8 | 8-12 | 12-24 | 0-24 |
| Adurix KCl | | | | | | | | | |
| 1 | -0.49 | 1.64 | 5.14 | 3.48 | 3.27 | 2.36 | 2.72 | 6.23 | 24.35 |
| 2 | -3.88 | 3.97 | 3.18 | 3.59 | 5.12 | 1.43 | 7.03 | 16.44 | 36.88 |
| 3 | -1.41 | 1.42 | 4.67 | 5.76 | 6.82 | 9.64 | 5.74 | 7.83 | 40.47 |
| 4 | -2.57 | -2.65 | -0.43 | 3.93 | 5.22 | 2.32 | 3.48 | 0.03 | 9.33 |
| 5. | 4.96 | 2.77 | 1.54 | 1.63 | 2.64 | 5.24 | 4.33 | 12.92 | 36.03 |
| 6. | 10.17 | 3.95 | 2.37 | 3.25 | 2.83 | 0.53 | 1.53 | -1.79 | 17.18 |
| 7 | 0.33 | 1.56 | 8.39 | -3.45 | 1.13 | 3.69 | 7.74 | 0.73 | 20.12 |
| 8 | 3.05 | 3.61 | 2.64 | 2.90 | 5.41 | -1.13 | 4.02 | 4.30 | 24.80 |
| 9 | 5.10 | 2.06 | 3.08 | 2.51 | 9.65 | 3.61 | 9.42 | 21.84 | 57.27 |
| 10 | -0.66 | 4.26 | -0.48 | 1.23 | 9.60 | 4.73 | 11.14 | 15.15 | 44.97 |
| Median | -0.03 | 2.42 | 2.86 | 3.08 | 5.17 | 2.99 | 5.04 | 7.03 | 30.43 |
| Average | | | | | | | | | 31.14 |
| s | | | | | | | | | 14.52 |
| Brinaldix + Kalinorm | | | | | | | | | |
| 1 | 2.28 | 0.40 | 1.55 | 2.19 | 5.02 | -2.27 | -0.33 | 3.69 | 12.53 |
| 2 | 2.15 | 3.83 | 5.05 | 3.82 | 5.51 | 1.34 | 4.62 | 10.22 | 36.54 |
| 3 | 4.04 | 3.38 | -0.80 | 4.76 | 8.92 | 2.51 | 2.21 | 10.34 | 35.36 |
| 4 | -0.50 | 0.81 | 0.29 | 1.11 | -2.69 | 2.22 | 0.46 | 1.61 | 3.31 |
| 5 | -1.12 | 0.08 | 1.90 | 0.32 | 3.37 | 5.20 | 3.64 | 10.82 | 24.21 |
| 6 | 5.74 | 4.64 | 6.02 | 2.02 | 7.53 | 2.96 | -4.28 | 2.83 | 27.46 |
| 7 | 1.39 | 2.33 | 2.14 | 4.89 | -0.32 | 0.03 | 3.00 | 9.93 | 23.39 |
| 8 | 4.44 | 4.41 | 3.15 | 7.17 | 7.62 | 4.74 | 10.14 | 5.62 | 47.29 |
| 9 | 0.53 | 1.69 | 1.97 | 3.08 | 4.33 | 6.90 | 4.80 | 12.70 | 36.00 |
| 10 | 0.03 | 1.28 | 4.10 | 3.25 | 6.16 | 6.99 | 14.19 | 18.11 | 54.11 |
| Median | 1.77 | 2.01 | 2.06 | 3.17 | 5.27 | 2.78 | 3.32 | 10.08 | 31.46 |
| Average | | | | | | | | | 30.02 |
| s | | | | | | | | | 15.24 |

The relative extent of availability of clopamide from Adurix KCl was 100,9% of that from Brinaldix, and the 95% confidence interval ranges from 93.1% to 109.4%.

The mean peak plasma concentration of clopamide after administration of a single dose of clopamide given as Adurix KCl and Brinaldix, respectively, was 228.9 μg/ml and 227.1 μg/ml. The relative peak height after Adurix KCl was 101.6% with a 95% confidence interval from 87.3% to 118.2%. Median time to peak was 1.5 hours after Adurix KCl and 2.0 hours after Brinaldix (FIG. 1 (where • indicates Adurix+KCl and ° indicates Brinaldix+Kalinorm)). No statistically significant differences between the formulations were seen, and Adurix KCl can therefore be stated to be bioequivalent to Brinaldix concerning clopamide.

The diuretic effect of clopamide 20 mg was clearly demonstrated since a statistically significant increase in 24 hours urine volume as well as hourly maximal urine volume was seen on treatment days compared to control days.

The total 24 h urine was 160.4%-95% confidence interval; 138.9 to 185.3% of that of control days. No significant differences between diuretic effect or diuretic profile after intake of clopamide in the two formulations were seen. The total amount of potassium excreted during 24 hours was identical after intake of 2400 mg (32 mEq) potassium as Adurix KCl and Kalinorm. The mean additional amount excreted, calculated as the difference between the amount excreted on control day and treatment day was 31.1 mEq after Adurix KCl and 30.0 mEq after Kalinorm (Table 4).

In the present study the concomitant administration of clopamide and potassium makes the use of "amounts of potassium excreted into urine" to a questionable

LITERATURE

Great Britain Pat. No. 1 468 172.
Eur. Patent Application No. 79 850 110, Publication No. 0 013 262.
U.S. Pat. No. 4,193,985.
Baggensen S., Bechgaard H., & Schmidt K. (1981). Content and dissolution uniformity testing of controlled-release products: The Repro-Dose® quality control procedure. *Pharm. Acta Helv* 56, 85-92.
Bechgaard, H. & Hegermann Nielsen, G. (1978) Controlled release multiple-units and single-units doses. A literature review. *Drug Develop Ind Pharm* 4, 53-67.
Bechgaard, H. & Ladefoged, K. (1978). Distribution of pellets in the gastrointestinal tract. The influence on transit time exerted by the density or diameter of pellets. *J. Pharm Pharmacol* 30, 690-692.
Bechgaard, H. & Baggesen, S. (1980). Propoxyphene and norpropoxyphene: Influence of type of controlled release formulation on intra- and intersubject variations. *J Pharm Sci* 69, 1327-1330.
Bogentoft, C., Carlsson, I., Ekenved, G. & Magnusson, A. (1978). Influence of food on the absorption of acetylsalicylic acid from enteric-coated dosage forms. *Eur J Clin Pharmacol* 14, 351-355.
Green, D. M. (1966). Tablets of coated aspirin microspherules—A new dosage form. *J New Drugs* 6, 294-303.
McDonald, P. J., Mather, L. E. & Story, M. J. (1977). Studies on absorption of a newly developed enteric-coated erythromycin base. *J Clin Pharmacol* 17, 601-606.

Snedecor, G. W. & Cochran, W. G. (1967). Statistical Methods. Iowa State University Press, Iowa, 271–275.
Pharmaceutical Dosage Forms. Tablets. Eds. Lieberman, H. A. & Lachman, L., vol. 2, Marcel Dekker, Inc., New York 1981.

We claim:

1. A pharmaceutical oral controlled release multiple-unit dosage form containing a multiplicity of individual coated units, each unit containing an active substance coated with a water-insoluble, but water diffusible controlled release coating, each unit additionally comprising particles of active substance adhered to the surface of the controlled release coating in a substantially uniform layer, the particles being at least one power of ten smaller than the coated unit.

2. A dosage form according to claim 1 in which the active substance adhered to the surface of the controlled release coating is present in an amount of no more than about 25% by weight.

3. A dosage form according to claim 2, wherein the active substance adhered to the surface of the controlled release coating is present in an amount of no more than 10% by weight, calculated on the weight of the coated units.

4. A dosage form according to claim 1, additionally comprising an anti-adhesive adhered to the coated units.

5. A dosage form according to claim 4, wherein the anti-adhesive is a fine particle powder which counteracts electrostatic charging.

6. A dosage form according to claim 1 in which the controlled release coating contains a film-forming substance, a plasticizer, and a hydrophobic substance.

7. A dosage form according to claim 6, wherein the plasticizer is selected from triacetin, acetylated monoglyceride, rape oil, olive oil, sesame oil, acetyltributylcitrate, acetyltriethylcitrate, glycerin, sorbitol, diethyloxyalate, diethylmalate, diethylfumarate, diethylsuccinate, diethylmalonate, dioctylphthalate, dibutylsebacate, triethylcitrate, tributylcitrate, glyceroltributyrate, polyethyleneglycol, propyleneglycol, and mixtures of the above.

8. A dosage form according to claim 6, wherein the hydrophobic substance is present in an amount of between about 1 and 25% calculated on the weight of the dry matter of the coating suspension.

9. A dosage form according to claim 8, wherein the hydrophobic substance is present in an amount of between 3 and 20%, calculated on the weight of dry matter of the coating suspension.

10. A dosage form according to claim 6, wherein the hydrophobic substance is selected from hydrocarbons and hydrocarbon derivatives, waxes, oils and fats, and mixtures thereof.

11. A dosage form according to claim 10, wherein the hydrophobic substance is a wax-like substance selected from beef tallow, whale wax, beeswax, paraffin wax and castor wax, and higher fatty acids and esters thereof.

12. A dosage form according to claim 1, wherein the film-forming substance is selected from cellulose derivatives, acrylic polymers, vinyl polymers, and other high molecular synthetic polymers.

13. A dosage form according to claim 1, wherein the units are crystals.

14. A dosage form according to claim 1, wherein the active substance in the units is potassium chloride.

15. A dosage form according to claim 14, wherein the potassium chloride is in the form of potassium chloride crystals, each unit substantially comprising one crystal.

16. A dosage form according to claim 1, in which the coated units are of a size between about 0.1 and 1.5 mm.

17. A dosage form according to claim 16, wherein the coated units are of a size between 0.4 and 1.0 mm.

18. A dosage form according to claim 1, in which the active substance which is present on the surface of the coating is present substantially as a monolayer.

19. A dosage form according to claim 1, in which the active substance in the coated units is potassium chloride and the active substance which is adhered to the surface of the controlled release coating is a diuretic.

20. A dosage form according to claim 1 which is a tablet which disintegrates substantially immediately upon ingestion in the stomach into a multiplicity of individual units.

21. A dosage form according to claim 1, wherein the active substance adhered to the surface of the controlled release coating is present in an amount of 0.5–1% by weight, calculated on the weight of the coated units.

22. A method for preparing a pharmaceutical oral controlled release multiple-unit dosage form, comprising mixing a multiplicity of individual units, each of which contains an active substance and is coated with a substantially water-insoluble, but water diffusible controlled release coating, with particles of an active substance the mean size of which is at least one power of 10 smaller than the coated units, under conditions which result in adherence of the smaller particles to the surface of the controlled release coating in a substantially uniform layer.

23. A method according to claim 22 in which the proportion of the smaller particles which are adhered to the controlled release coating in the mixing process is no more than about 25% by weight, calculated on the weight of coated units.

24. A method according to claim 23 in which the mixing is performed in the presence of an anti-adhesive which counteracts undesired attraction between the small particles and between the small particles and the mixing equipment.

25. A method according to claim 24 in which the anti-adhesive is a fine particle powder of a kind which counteracts static charging.

26. A method according to claim 23, wherein the proportion of the smaller particles which are adhered to the controlled release coating in the mixing process is 0.5–1% by weight, calculated on the weight of the coated units.

27. A method according to claim 22 in which the coated units are of a mean size of between about 0.1 and 1.5 mm, and the fine particles have a mean particle size as measured by microscopy, of from about 1 to about 50 μm.

28. A method according to claim 22 in which the mixing is performed in low shear mixing equipment or cube mixers.

29. A method according to claim 22 in which the units with applied small particles adhering to the controlled release coating are combined with excipients and compressed into disintegratable tablets.

* * * * *